(12) United States Patent
Chen et al.

(10) Patent No.: US 9,707,385 B1
(45) Date of Patent: Jul. 18, 2017

(54) TATTOO NEEDLE TUBE AND GRIP ADAPTER

(71) Applicants: Michael Chen, Baldwin Park, CA (US); Adam Miller, Los Angeles, CA (US)

(72) Inventors: Michael Chen, Baldwin Park, CA (US); Adam Miller, Los Angeles, CA (US)

(73) Assignee: IMPORTLA, LLC, Baldwin Park, CA (US)

( * ) Notice: Subject to any disclaimer, the term of this patent is extended or adjusted under 35 U.S.C. 154(b) by 194 days.

(21) Appl. No.: 14/538,316

(22) Filed: Nov. 11, 2014

(51) Int. Cl.
| F16L 21/00 | (2006.01) |
| A61M 37/00 | (2006.01) |
| A61M 39/10 | (2006.01) |

(52) U.S. Cl.
CPC .... *A61M 37/0076* (2013.01); *A61M 39/1011* (2013.01); *A61M 2039/1077* (2013.01)

(58) Field of Classification Search
USPC .......................................... 285/90, 403, 404
See application file for complete search history.

(56) References Cited

U.S. PATENT DOCUMENTS

| 3,107,107 | A | * | 10/1963 | Guarnaschelli | F16L 27/082 277/379 |
| 4,133,350 | A | * | 1/1979 | Nelson | B05B 15/065 138/44 |
| 6,817,895 | B2 | * | 11/2004 | Kiely | H01R 9/2475 439/488 |
| 7,126,064 | B1 | * | 10/2006 | Shemtov | H01R 13/5812 174/650 |
| 7,151,223 | B2 | * | 12/2006 | Auray | H01R 4/646 174/480 |
| 7,161,095 | B1 | * | 1/2007 | Gretz | H02G 3/0666 16/2.1 |
| 7,495,184 | B1 | * | 2/2009 | Gretz | H01R 13/5812 16/2.1 |
| 8,646,813 | B1 | * | 2/2014 | Shemtov | F16L 25/0036 174/60 |
| 2007/0152441 | A1 | * | 7/2007 | Jennings | E21B 17/085 285/90 |

* cited by examiner

*Primary Examiner* — Aaron Dunwoody
(74) *Attorney, Agent, or Firm* — Hankin Patent Law, APC; Kevin Schraven; Anooj Patel

(57) ABSTRACT

An adapter for fixing a traditional tattoo needle tube and grip with a tattoo machine of the type having a threaded collar includes a tube holder having a longitudinal bore, a nut-retaining flange at a proximal end thereof, and a tube retaining mechanism at a distal end thereof. A first threaded nut is retained by the nut-retaining flange at the proximal end of the tube holder and adapted for fixing with the threaded collar of the tattoo machine. As such, with the first threaded nut fixed with the threaded collar of the tattoo machine, and with the tattoo needle tube and grip fixed with the tube holder by the tube retaining mechanism, the tattoo needle tube and grip are fixed with the tattoo machine.

10 Claims, 5 Drawing Sheets

TATTOO NEEDLE TUBE AND GRIP ADAPTER

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to tattoo machines, and more particularly to an adapter for allowing a traditional tattoo needle tube and grip to be used with a non-standard tattoo machine.

DISCUSSION OF RELATED ART

Tattoo machines of the type having a threaded collar for fixing with a combination threaded nut and grip, such as those sold under the brand name Cheyenne by MT.DERM GmbH of Berlin, Germany, are not easily adapted for use with the traditional tattoo needle tube and grip. However, often the proprietary threaded nut and grip that can be used with such a machine is not readily available or is overpriced in the marketplace.

Therefore, there is a need for a device that allows a traditional tattoo needle tube and grip to be used with such a proprietary tattoo machine. Such a needed invention would be relatively simple to install and use, and would be relatively inexpensive to manufacture. Further, such a needed device would be readily removable from the tattoo machine if the operator wishes to use the tattoo machine with the proprietary type of threaded nut and grip. The present invention accomplishes these objectives.

SUMMARY OF THE INVENTION

The present device is an adapter for fixing a traditional tattoo needle tube and grip with a tattoo machine of the type having a threaded collar for fixing with a combination threaded nut and grip. The adapter includes a tube holder having a longitudinal bore, a nut-retaining flange at a proximal end thereof, and a tube retaining mechanism at a distal end thereof.

A first threaded nut is retained by the nut-retaining flange at the proximal end of the tube holder and adapted for fixing with the threaded collar of the tattoo machine. Preferably the first threaded nut includes a knurled outer surface.

Preferably the tube retaining mechanism includes at least one traverse aperture in the distal end of the tube holder. Each transverse aperture is adapted to receive a pressure arm therethrough, each pressure arm adjustably slidable within the transverse aperture to press against the tattoo needle tube and within the longitudinal bore to fix the tattoo needle tube and grip within the adapter.

In one embodiment, the at least one pressure arm is slidably fixed within the distal end of the tube holder with a second threaded nut rotationally fixed about a central threaded shaft rotationally fixed to the tube holder. Such a threaded shaft may include a tool-receiving head formed in distal end thereof, such that the threaded shaft may be screwed into the tube holder with an Allen wrench, screwdriver, or the like. The second threaded nut may be a wing nut or a threaded nut.

Alternately, the at least one pressure arm is slidably fixed with the distal end of the tube holder with a threaded screw that is rotationally engaged to a threaded transverse aperture in the tube holder. In such an embodiment, the length of the threaded screw is less than the length of each pressure arm so that each pressure arm contacts the needle tube before the threaded screw.

Preferably the at least one pressure arm includes exactly two pressure arms, each of which includes a curved distal end adapted for pressing evenly against the tattoo needle tube within the longitudinal bore of the tube holder so as to reduce the chance of the tattoo needle tube breaking under the pressure applied thereto by the pressure arms.

As such, with the first threaded nut fixed with the threaded collar of the tattoo machine, and with the tattoo needle tube and grip fixed with the tube holder by the tube retaining mechanism, the tattoo needle tube and grip are fixed with the tattoo machine.

While a particular form of the invention has been illustrated and described, it will be apparent that various modifications can be made without departing from the spirit and scope of the invention. Accordingly, it is not intended that the invention be limited, except as by the appended claims.

The present invention allows a traditional tattoo needle tube and grip to be used with a proprietary tattoo machine of the type having a threaded collar. The present device is relatively simple to install and use, and is relatively inexpensive to manufacture. Further, the present device is readily removable from the tattoo machine if the operator wishes to use the tattoo machine with the proprietary type of threaded nut and grip. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 2:
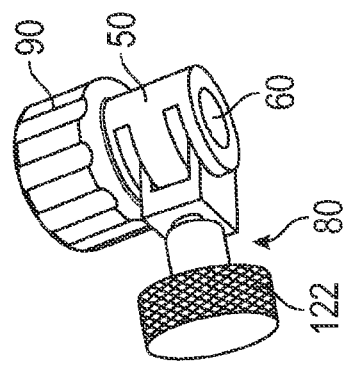
FIG. 2 is a perspective view of the adapter of the invention.
Figure 1:
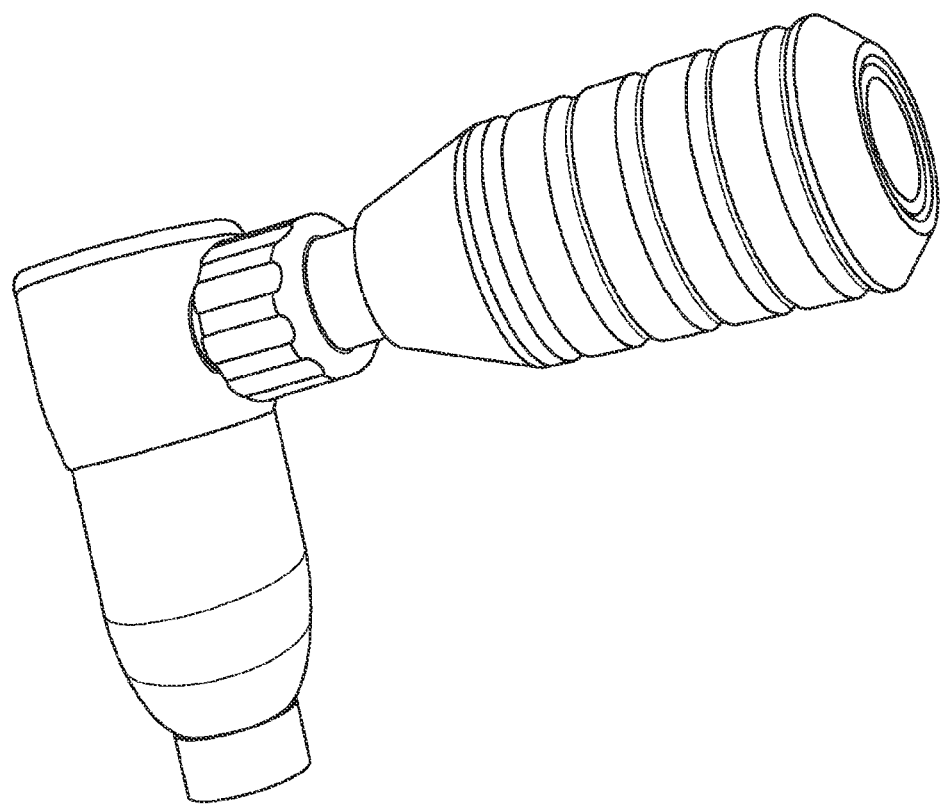
FIG. 1 is a perspective view of a prior art tattoo machine of the type having a threaded collar for fixing with a combination threaded nut and grip.

FIGS. 1 and 2 illustrate an adapter 10 for fixing a traditional tattoo needle tube and grip 20 with a tattoo machine 30 of the type having a threaded collar 32 for fixing with a combination threaded nut and grip 33, sold under the brand name Cheyenne by MT.DERM GmbH of Berlin, Germany.

Figure 3:
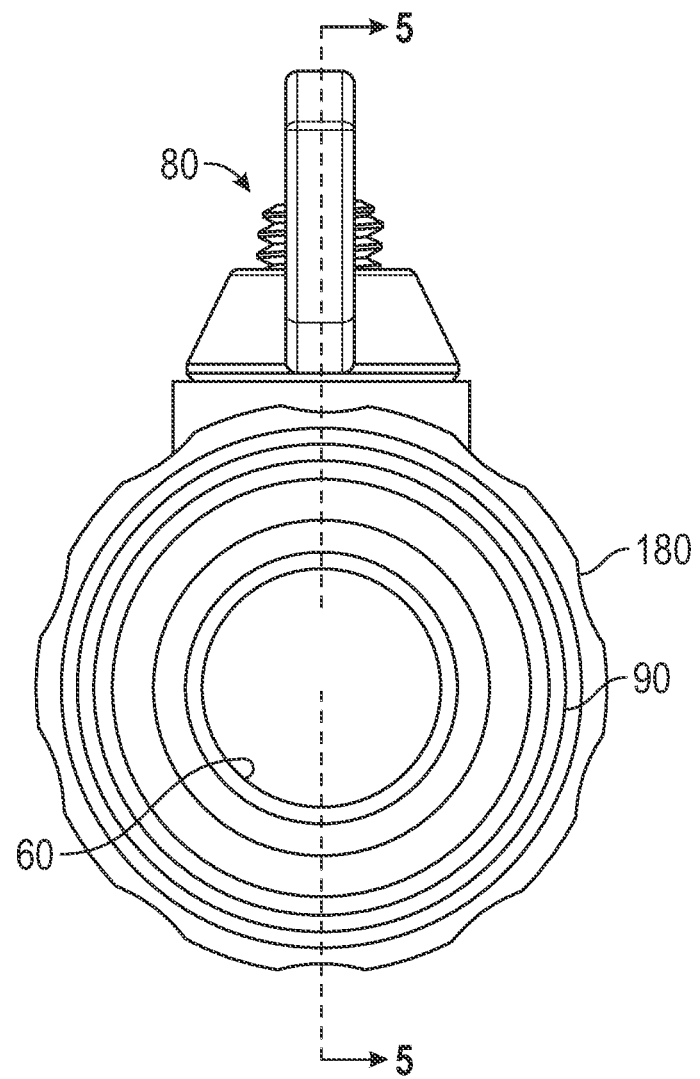
FIG. 3 is a front elevational view of the invention.
Figure 4:
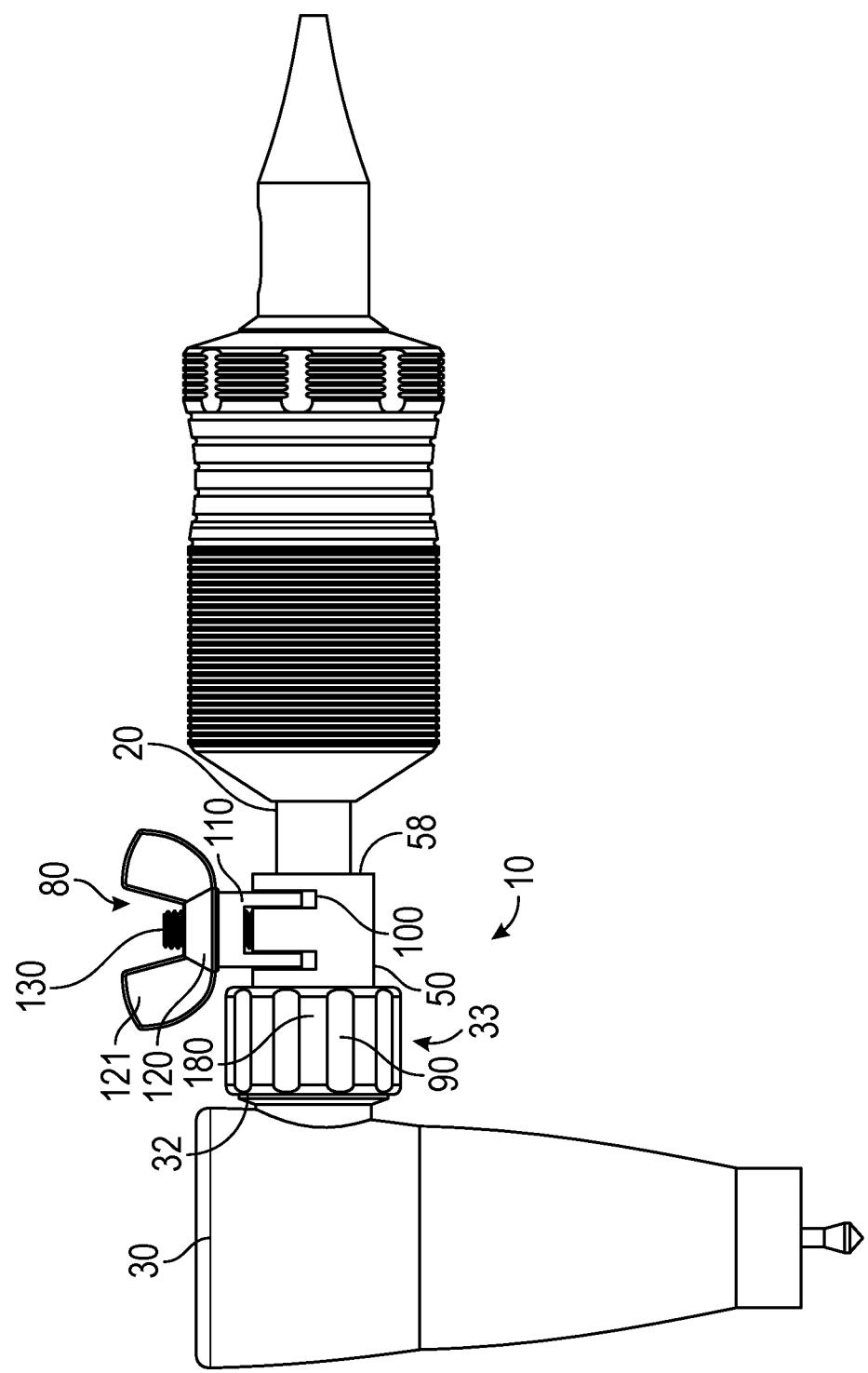
FIG. 4 is a side elevational view of the invention as fixed with the tattoo machine and grip.

The adapter 10 includes a tube holder 50 having a longitudinal bore 60 (FIGS. 2 and 3), a nut-retaining flange 70 (FIG. 5) at a proximal end 52 thereof, and a tube retaining mechanism 80 at a distal end 58 thereof. The tube holder 50 is preferably made with a rigid injection-molded plastic or metal material.

Figure 6:
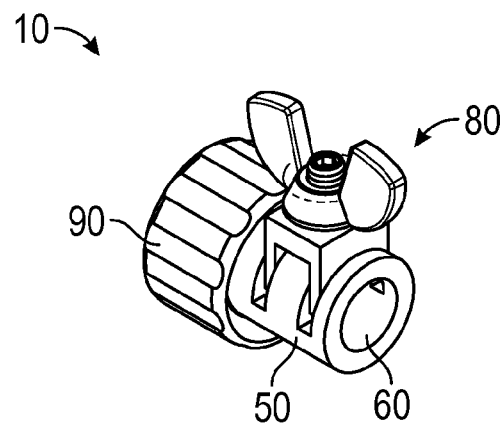
FIG. 6 is a perspective view of an alternate embodiment of the invention.

A first threaded nut 90 (FIGS. 2 and 6) is retained by the nut-retaining flange 70 at the proximal end 52 of the tube holder 50 and adapted for fixing with the threaded collar 32 of the tattoo machine 30. Preferably the first threaded nut 90 includes a knurled outer surface 180.

Preferably the tube retaining mechanism 80 includes at least one traverse aperture 100 in the distal end 58 of the tube holder 50. Each transverse aperture 100 is adapted to receive a pressure arm 110 therethrough, each pressure arm 110 adjustably slidable within the transverse aperture 100 to press against the tattoo needle tube and 20 within the longitudinal bore 60 to fix the tattoo needle tube and grip 20 within the adapter 10. Each pressure arm 110 is preferably a rigid, plastic or metal material.

Figure 7:
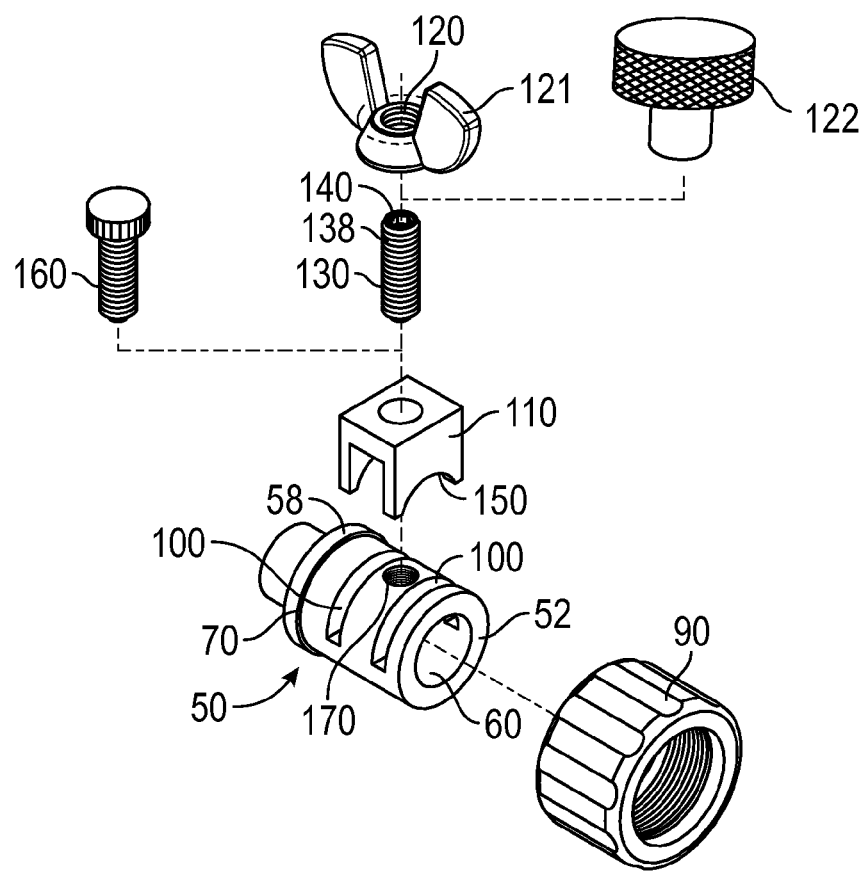
FIG. 7 is an exploded view of the embodiment of FIG. 6.

In one embodiment, the at least one pressure arm 110 is slidably fixed within the distal end 58 of the tube holder 50 with a second threaded nut 120 rotationally fixed about a central threaded shaft 130 rotationally fixed to the tube holder 50. Such a threaded shaft 130 may include a tool-receiving head 140 formed in distal end 138 thereof, such that the threaded shaft may be screwed into the tube holder 50 with an Allen wrench (not shown), screwdriver, or the like. The second threaded nut 120 may be a wing nut 121 (FIGS. 3-7), or a threaded nut 122 (FIGS. 2 and 7).

Alternately, the at least one pressure arm 110 is slidably fixed with the distal end 58 of the tube holder 50 with a threaded screw 160 (FIG. 7) that is rotationally engaged to a threaded transverse aperture 170 in the tube holder 150. In such an embodiment, the length of the threaded screw 160 is less than the length of each pressure arm 110 so that each pressure arm 110 contacts the needle tube 20 before the threaded screw 160.

Preferably the at least one pressure arm incudes exactly two pressure arms 110, each of which includes a curved distal end 150 (FIG. 7) adapted for pressing evenly against the tattoo needle tube 20 within the longitudinal bore 160 of the tube holder 150 so as to reduce the chance of the tattoo needle tube 20 breaking under the pressure applied thereto by the pressure arms 110.

Figure 5:
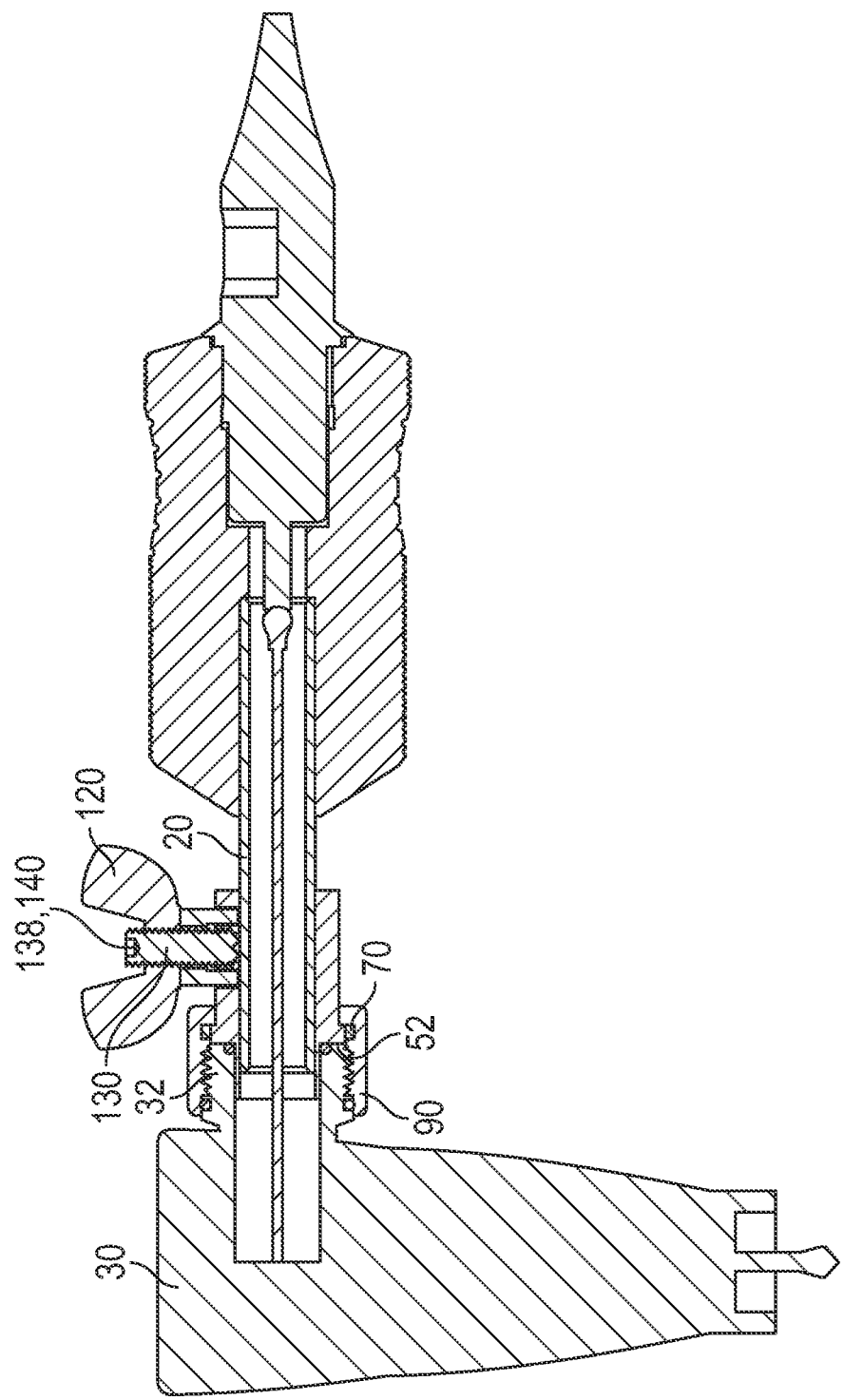
FIG. 5 is a cross-sectional view of the invention, taken generally along line 5-5 of FIG. 3.

As such, with the first threaded nut 90 fixed with the threaded collar 32 of the tattoo machine 30, and with the tattoo needle tube and grip 20 fixed with the tube holder 50 by the tube retaining mechanism 80, the tattoo needle tube and grip 20 are fixed with the tattoo machine 30 (FIG. 5).

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. An adapter for fixing a traditional tattoo needle tube and grip with a tattoo machine having a threaded collar for fixing with a combination threaded nut and grip, the adapter including:
- a tube holder having a longitudinal bore, a nut-retaining flange at a proximal end thereof, and a tube retaining mechanism at a distal end thereof; and
- a first threaded nut retained by the nut-retaining flange at the proximal end of the tube holder and adapted for fixing with the threaded collar of the tattoo machine; and—
- the tube retaining mechanism including at least one transverse aperture in the distal end of the tube holder, each adapted to receive a pressure arm therethrough, each pressure arm adjustably slidable within the transverse aperture to press against the tattoo needle tube within the longitudinal bore to fix the tattoo needle tube within the adapter;
- the at least one pressure arm slidably fixed with the distal end of the tube holder with a second threaded nut rotationally fixed about a central threaded shaft rotationally fixed to the tube holder;
- the second threaded nut being a wing nut;
- whereby with the first threaded nut adapted to be fixed with the threaded collar of the tattoo machine, and with the tattoo needle tube and grip adapted to be fixed with the tube holder by the tube retaining mechanism, the tattoo needle tube and grip may be fixed with the tattoo machine.

2. The adapter of claim 1 wherein the threaded shaft includes a tool-receiving head formed in a distal end thereof.

3. The adapter of claim 1 wherein the at least one pressure arm includes exactly two pressure arms, and wherein each pressure arm includes a curved distal end adapted for pressing against the tattoo needle tube within the longitudinal bore of the tube holder.

4. The adapter of claim 1 wherein the at least one pressure arm is slidably fixed with the distal end of the tube holder with a threaded screw that is rotationally engaged to a threaded transverse aperture in the tube holder, whereby a head of the threaded screw as tightened applies pressure to each pressure arm and, in turn, to the tattoo needle tube within the longitudinal bore.

5. The adapter of claim 1 wherein the first threaded nut includes a knurled outer surface.

6. An adapter for fixing a traditional tattoo needle tube and grip with a tattoo machine having a threaded collar for fixing with a combination threaded nut and grip, the adapter including:
- a tube holder having a longitudinal bore, a nut-retaining flange at a proximal end thereof, and a tube retaining mechanism at a distal end thereof; and
- a first threaded nut retained by the nut-retaining flange at the proximal end of the tube holder and adapted for fixing with the threaded collar of the tattoo machine; and—
- the tube retaining mechanism including at least one transverse aperture in the distal end of the tube holder, each adapted to receive a pressure arm therethrough, each pressure arm adjustably slidable within the transverse aperture to press against the tattoo needle tube within the longitudinal bore to fix the tattoo needle tube within the adapter;
- the at least one pressure arm slidably fixed with the distal end of the tube holder with a second threaded nut rotationally fixed about a central threaded shaft rotationally fixed to the tube holder;
- the second threaded nut being a knurled nut;
- whereby with the first threaded nut adapted to be fixed with the threaded collar of the tattoo machine, and with the tattoo needle tube and grip adapted to be fixed with the tube holder by the tube retaining mechanism, the tattoo needle tube and grip may be fixed with the tattoo machine.

7. The adapter of claim 6 wherein the threaded shaft includes a tool-receiving head formed in a distal end thereof.

8. The adapter of claim 6 wherein the at least one pressure arm includes exactly two pressure arms, and wherein each pressure arm includes a curved distal end adapted for pressing against the tattoo needle tube within the longitudinal bore of the tube holder.

9. The adapter of claim 6 wherein the at least one pressure arm is slidably fixed with the distal end of the tube holder with a threaded screw that is rotationally engaged to a threaded transverse aperture in the tube holder, whereby a head of the threaded screw as tightened applies pressure to each pressure arm and, in turn, to the tattoo needle tube within the longitudinal bore.

10. The adapter of claim 6 wherein the first threaded nut includes a knurled outer surface.

* * * * *